United States Patent [19]

Ramesh et al.

[11] Patent Number: 5,672,703

[45] Date of Patent: Sep. 30, 1997

[54] 1,3,5-TRIAZINE COMPOUNDS SUBSTITUTED WITH ACETAL AND/OR CYCLIZED ACETAL-BASED GROUPS

[75] Inventors: Subban Ramesh, Parsippany, N.J.; Laurence Lyman Williams, Stamford, Conn.; Ram Baboo Gupta, Bronx, N.Y.; Lon-Tang Wilson Lin, Bethel, Conn.

[73] Assignee: Cytec Technology Corp., Wilmington, Del.

[21] Appl. No.: 408,323

[22] Filed: Mar. 21, 1995

[51] Int. Cl.⁶ .................................. C07D 251/40
[52] U.S. Cl. .................. 544/194; 540/598; 544/113; 544/198; 544/207
[58] Field of Search .................. 544/194, 198, 544/207, 113; 540/598

[56] References Cited

U.S. PATENT DOCUMENTS

| | | | |
|---|---|---|---|
| 3,270,014 | 8/1966 | Urspurng et al. | 544/194 |
| 3,542,752 | 11/1970 | Hoffman et al. | 544/194 |
| 4,467,089 | 8/1984 | Bechara | 544/351 |
| 4,647,611 | 3/1987 | Goldstein et al. | 524/458 |
| 4,663,410 | 5/1987 | Pinschmidt, Jr. et al. | 526/263 |
| 4,691,026 | 9/1987 | Pinschmidt, Jr. et al. | 548/531 |
| 4,774,283 | 9/1988 | Goldstein | 524/816 |
| 4,788,288 | 11/1988 | Pinschmidt, Jr. et al. | 544/212 |
| 4,814,226 | 3/1989 | Goldstein | 428/288 |
| 4,864,055 | 9/1989 | Pinschmidt, Jr. et al. | 560/160 |
| 4,939,213 | 7/1990 | Jacobs, III et al. | 525/329.9 |
| 4,959,489 | 9/1990 | Nordquist et al. | 560/170 |
| 5,084,541 | 1/1992 | Jacobs, III et al. | 528/45 |
| 5,288,865 | 2/1994 | Gupta | 544/200 |
| 5,298,567 | 3/1994 | Burgoyne, Jr. et al. | 525/327.6 |

FOREIGN PATENT DOCUMENTS

| | | |
|---|---|---|
| A 0024254 | 2/1981 | European Pat. Off. |
| A-0218827 | 7/1986 | European Pat. Off. |
| A 0218827 | 4/1987 | European Pat. Off. |
| 58-146582 | 9/1983 | Japan |
| WO 9310117 | 5/1993 | WIPO |

OTHER PUBLICATIONS

R.K. Pinschmidt, Jr. et al., "Amide-Blocked Aldehyde--Functional Monomers", *American Chem. Soc. Symp. Ser., Crosslinked Polymers*, vol. 367, pp. 453–466 (1988).

K. Kjellqvist et al., "Surface Reactive Acetal Functional Waterborne Microparticles," *J. Appl. Polym. Science*, vol. 51, pp. 1063–1070 (1994).

CA73: 108869, 1970.

CA71: 21385, 1969.

CA67: 73624, 1966.

*Primary Examiner*—Yogendra N. Gupta
*Attorney, Agent, or Firm*—Bart E. Lerman; Claire M. Schultz; Michael J. Kelly

[57] ABSTRACT

New classes of 1,3,5-triazine compounds and compositions containing the same are disclosed, which compounds are of the general formula

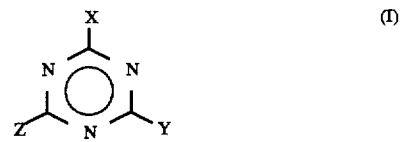

wherein each of Y, Z and optionally X are independently selected from a group of the formula (II), (III) and/or (IV)

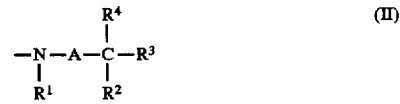

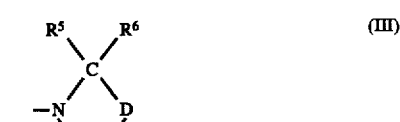

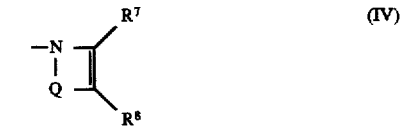

These compounds and compositions are particularly suitable for use as crosslinking agents in curable compositions such as coatings, particularly in combination with active hydrogen groups-containing materials. The 1,3,5-triazine compounds of the present invention do not release formaldehyde as a volatile by-product during cure, and certain of these compounds may be used in curable compositions which may be cured at relatively low temperature. Processes for preparing such compounds, compositions containing the same, as well as additional uses thereof, are also disclosed.

22 Claims, No Drawings

1,3,5-TRIAZINE COMPOUNDS SUBSTITUTED WITH ACETAL AND/OR CYCLIZED ACETAL-BASED GROUPS

BACKGROUND OF THE INVENTION

1. Field of the Invention

This invention relates to the preparation of compounds and compositions which are particularly suitable for use as crosslinking agents in curable compositions, and especially coatings, which are capable of curing at lower temperatures, and which do not release formaldehyde as a volatile by-product when cured.

2. Description of Related Art

Various derivatives of amino-1,3,5-triazines are described in the literature as being utilized in a wide variety of fields. An important use of some triazine derivatives, such as the alkoxyalkyl derivatives of melamine and guanamine, is based upon their ability to act as crosslinking agents in curable compositions containing resins which contain active hydrogen groups. While alkoxyalkylated melamines and guanamines provide excellent results in some respects, they do have the disadvantage of releasing formaldehyde as a volatile by-product under cure conditions. Because of this, it has long been a desire of industry to find acceptable alternatives which do not emit formaldehyde during cure.

A recently discovered non-formaldehyde alternative which has shown great promise is the class of isocyanate and carbamate-functional 1,3,5-triazine crosslinking agents disclosed in the commonly owned U.S. Pat. Nos. 4,939,213, 5,084,541 and 5,288,865, which are incorporated by reference herein for all purposes as if fully set forth. The isocyanate and carbamate functional 1,3,5-triazines disclosed therein are efficient non-formaldehyde emitting crosslinking agents which are particularly useful in curable coating compositions.

Another non-formaldehyde alternative which utilizes addition chemistry in crosslinking polyfunctional active hydrogen containing compounds is the class of 2,4,6-trislactam substituted 1,3,5-triazine crosslinking agents disclosed in EP-A-0570563, which is also incorporated by reference herein for all purposes as if fully set forth. The tris-lactam crosslinkers disclosed therein are efficient non-formaldehyde emitting crosslinking agents which are particularly useful in curable powder coating compositions.

Still another alternative is described in U.S. Pat. No. 4,647,611, U.S. Pat. No. 4,663,410, U.S. Pat. No. 4,691,026, U.S. Pat. No. 4,774,283, U.S. Pat. No. 4,788,288, U.S. Pat. No. 4,814,226, U.S. Pat. No. 4,864,055, U.S. Pat. No. 4,959,489, U.S. Pat. No. 5,298,567, EP-A-0218827, an article by R. K. Pinschmidt, Jr., et al. in Amer. Chem. Soc. Symp. Ser., Crosslinked Polymers, Volume 367, page 453 (1988) and an article by K. Kjellqvist et al. in J. Appl. Polym. Science, Volume 51, page 1063 (1994), all of which are also incorporated herein by reference for all purposes as if fully set forth. These references disclose N-olefinically unsaturated ketals and acetals, and polymers and copolymers thereof, usable as non-formaldehyde generating crosslinking agents.

While some of these systems have shown great promise, the search continues for additional crosslinkers which emit little or no formaldehyde during cure.

We have now discovered new classes of compounds which are prepared without formaldehyde, and which function as highly compatible crosslinking agents. Films having good appearance, solvent resistance and gloss characteristics can be produced from coating compositions utilizing the crosslinking agents in accordance with the present invention. Certain of these crosslinkers may additionally produce fully cured films at very low temperatures, typically in the range of from about 50° C. to about 90° C. (although higher temperatures may also be utilized), without the need for catalysts (although catalysts may also be utilized) such as acids often required for amine-formaldehyde crosslinkers.

SUMMARY OF THE INVENTION

As indicated above, the present invention relates to compounds and compositions suitable for use as highly resin-compatible crosslinking agents which do not emit formaldehyde as a volatile by-product during cure.

The present inventive compounds may be represented by the following formula (I):

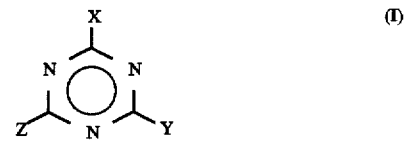

wherein

X is selected from the group consisting of hydrogen, halogen, alkyl, aralkyl, aryl, alkoxy, aralkoxy, aryloxy, alkylthio, aralkylthio, arylthio, amido, sulfonamido, sulfonate, amino, a group of the formula (II), a group of the formula (III), and a group of the formula (IV)

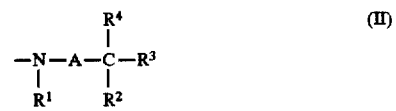

wherein

A is an alkylene group, $R^1$ is selected from the group consisting of hydrogen and a hydrocarbyl, $R^2$ is selected from the group consisting of hydrogen, a hydrocarbyl, —$OR^9$ and —$SR^{10}$, $R^3$ is selected from the group consisting of hydrogen, a hydrocarbyl, —$OR^9$ and —$SR^{10}$, and $R^4$ is selected from the group consisting of —$OR^{11}$ and —$SR^{12}$, with the proviso that at least one of $R^2$ and $R^3$ is selected from the group consisting of —$OR^9$ and —$SR^{10}$,

wherein

D is an alkylene group, $R^5$ is selected from the group consisting of hydrogen, a hydrocarbyl, —$OR^9$ and —$SR^{10}$, and $R^6$ is selected from the group consisting of hydrogen, a hydrocarbyl, —$OR^9$ and —$SR^{10}$, with the proviso that at least one of $R^5$ and $R^6$ is selected from the group consisting of —$OR^9$ and —$SR^{10}$,

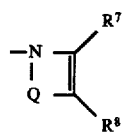

(IV)

wherein

Q is an alkylene group,

R$^7$ is selected from the group consisting of hydrogen, a hydrocarbyl, —OR$^9$ and —SR$^{10}$, and R$^8$ is selected from the group consisting of hydrogen and a hydrocarbyl, wherein each R$^9$ is independently selected from the group consisting of hydrogen and a hydrocarbyl, or together with R$^{11}$ forms a hydrocarbylene group, each R$^{10}$ is a hydrocarbyl, or together with R$^{12}$ forms a hydrocarbylene group, each R$^{11}$ is independently selected from the group consisting of hydrogen and a hydrocarbyl, or together with R$^9$ forms a hydrocarbylene group, each R$^{12}$ is a hydrocarbyl, or together with R$^{10}$ forms a hydrocarbylene group, with the proviso that, other than in a group of the formula (II), (III) or (IV) X contains no olefinic unsaturation; and wherein each of Y and Z is independently selected from the group consisting of a group of the formula (II), a group of the formula (III) and a group of the formula (IV).

This invention also includes a process for preparing derivatives of 1,3,5-triazines, including those of the formula (I) described above, which process comprises the step of contacting:

(i) a 1,3,5-triazine derivative represented by the formula (V) or an oligomer thereof:

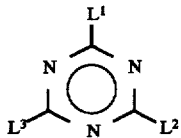

(V)

wherein

L$^1$ is selected from the group consisting of hydrogen, halogen, alkyl, aralkyl, aryl, alkoxy, aralkoxy, aryloxy, alkylthio, aralkylthio, arylthio, amido, sulfonamido, sulfonate, amino and a leaving group not previously mentioned, and each of L$^2$ and L$^3$ is independently a leaving group; and (ii) a nucleophilic reagent selected from the group consisting of a compound of the formula (VI), a compound of the formula (VII), a compound of the formula (VIII), a salt thereof and mixtures thereof:

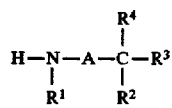

(VI)

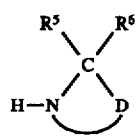

(VII)

-continued

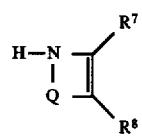

(VIII)

wherein

R$^1$–R$^{12}$, A, D and Q are as defined above, and wherein said contacting is carried out at a temperature and length of time sufficient to produce a 1,3,5-triazine derivative having thereon on average at least two groups derived from the nucleophilic reagent.

The present invention further includes a process for preparing derivatives of 1,3,5-triazines, including those of the formula (I) described above containing groups of the formula (III), which process comprises the steps of (a) contacting (i) a 1,3,5-triazine derivative represented by the formula (V) or an oligomer thereof, with (ii) a nucleophilic reagent of the formula (VI) or a salt thereof, at a temperature and length of time sufficient to produce a 1,3,5-triazine derivative having thereon on average at least two open-chain groups derived from the nucleophilic agent; then (b) intramolecularly cyclizing at least a portion of the open-chain groups.

The present invention further includes a process for preparing derivatives of 1,3,5-triazines, including those of the formula (I) described above containing groups of the formula (IV), which process comprises the step of eliminating from a 1,3,5-triazine derivative of the formula (I) containing a group of the formula (III), the element of HOR$^9$ from the group of the formula (III).

The present invention also relates to compositions obtainable by the processes as described above. Such compositions may comprise a complex mixture of compounds, including but not limited to compounds of the formula (I) as well as oligomeric versions thereof, but which in any event contain on average at least two groups of the formula (II), (III) and/or (IV) per molecule. Oligomers of the compounds of the formula (I), wherein X is a leaving group, may also be prepared by reacting such with a compound containing at least two active hydrogen groups, such as a diol or polyol, or diamine or polyamine.

The present invention further includes a curable composition, comprising: (a) a crosslinker component comprising the 1,3,5-triazine compound of the formula (I); and (b) a polyfunctional material containing on average at least two groups with active hydrogen functionality and/or functionality convertible thereto. The compositions prepared by the processes described above, of course, may function as the crosslinker component since they comprise compositions of the formula (I).

The present invention also relates to coating compositions based upon the above curable compositions, methods for coating substrates with such coating compositions, substrates so coated therewith, crosslinked films or objects derived from the curable compositions, and various end uses thereof.

Unlike hydroxyalkylated and alkoxyalkylated aminoplast derived crosslinking agents which (i) are prepared using formaldehyde, (ii) contain varying levels of free formaldehyde, and (iii) release formaldehyde during cure, the crosslinkers of the present invention have the advantage of containing no functionality capable of releasing formaldehyde during heat cure. Certain of the present crosslinkers, and particularly those containing cyclic groups of the formula (III), also have the advantage of producing coatings which may be fully cured at very low temperatures, typically in the range of about 50° C. to about 90° C. (although higher temperatures may also be utilized), without the need to use cure catalysts (although such may also be used). Cured films having good appearance, excellent thermal and ultraviolet (UV) light stability, good outdoor weatherability, good solvent resistance and high gloss can be produced from such coatings.

These and other features and advantages of the present invention will be more readily understood by those skilled in the relevant art from a reading of the following detailed description.

DETAILED DESCRIPTION OF THE PREFERRED EMBODIMENTS

As indicated above, the present invention relates most broadly to compounds of the formula (I). In this formula (I), and in the broadest context of the present invention, the following terms are given the meanings as set forth below:

"Alkyl" includes, for example, linear, branched, cyclic and alkyl substituted cyclic alkyls.

"Aryl" includes, for example, phenyl, other aryls as well as alkyl substituted aryls (alkaryl).

"Amido" includes, for example, both substituted and unsubstituted amidos, such as alkyl and/or aryl substituted amido groups.

"Amino" includes, for example, amino, alkyl and/or aryl substituted aminos, and heterocyclic N-containing groups optionally containing a different heteroatom in the ring structure. As examples of non-cyclic amino groups may be mentioned an amino group, a monoalkylamino, a monoaralkylamino, a monoarylamino, a dialkylamino, a diaralkylamino and a diarylamino. As examples of the cyclic amino groups may be mentioned substituted and unsubstituted pyrrolidino, piperidino, azepino, piperizino and morpholino groups.

"Hydrocarbyl" broadly refers to a group which contains at least carbon and hydrogen atoms and includes, for example, alkyl, aryl, aralkyl, alkenyl, and substituted derivatives thereof.

Preferred compounds of the general formula (I) are those wherein:

X is selected from the group consisting of hydrogen, alkyl of 1 to 8 carbon atoms, aryl of 6 to 10 carbon atoms, aralkyl of 7 to 14 carbon atoms, alkoxy of 1 to 8 carbon atoms, aryloxy of 6 to 10 carbon atoms, aralkoxy of 7 to 14 carbon atoms, alkylthio of 1 to 8 carbon atoms, arylthio of 6 to 10 carbon atoms, aralkylthio of 7 to 14 carbon atoms, amido of 1 to 8 carbon atoms, sulfonamido of 1 to 8 carbon atoms, amino ($-NH_2$), monoalkylamino of 1 to 8 carbon atoms, dialkylamino of 2 to 16 carbon atoms, pyrrolidino, piperidino, azepino, morpholino, N-alkylpiperazino, a group of the formula (II), a group of the formula (III) and a group of the formula (IV);

more preferably selected from the group consisting of a group of the formula (II), a group of the formula (III) and a group of the formula (IV), and especially selected from the group consisting of a group of the formula (II) and a group of the formula (III);

A is an alkylene group of 1 to 8 carbon atoms, and more preferably an alkylene group of 3 to 8 carbon atoms, and especially an alkylene group of 3 to 5 carbon atoms;

$R^1$ is selected from the group consisting of hydrogen and an alkyl of 1 to 8 carbon atoms;

$R^2$ is selected from the group consisting of hydrogen, an alkyl of 1 to 8 carbon atoms and $-OR^9$;

$R^3$ is selected from the group consisting of hydrogen, an alkyl of 1 to 8 carbon atoms and $-OR^9$;

$R^4$ is $-OR^{11}$;

with the proviso that at least one of $R^2$ and $R^3$ is a group $-OR^9$, and especially only one of $R^2$ and $R^3$ is a group $-OR^9$;

D is an alkylene group of 3 to 8 carbon atoms, and more preferably an alkylene group of 3 to 5 carbon atoms;

$R^5$ is selected from the group consisting of hydrogen, an alkyl of 1 to 8 carbon atoms and $-OR^9$;

$R^6$ is selected from the group consisting of hydrogen, a an alkyl of 1 to 8 carbon atoms and $-OR^9$;

with the proviso that at least one of $R^5$ and $R^6$ is $-OR^9$, and especially only one of $R^5$ and $R^6$ is a group $-OR^9$;

Q is an alkylene group of 2 to 7 carbon atoms, more preferably an alkylene group of 2 to 4 carbon atoms;

$R^7$ is selected from the group consisting of hydrogen, an alkyl of 1 to 8 carbon atoms and $-OR^9$, and more preferably selected from hydrogen and an alkyl of 1 to 8 carbon atoms;

$R^8$ is selected from the group consisting of hydrogen and an alkyl of 1 to 8 carbon atoms;

each $R^9$ is independently selected from the group consisting of hydrogen and an alkyl of 1 to 8 carbon atoms, or together with $R^{11}$ forms an alkylene group of 2 to 8 carbon atoms, each $R^{11}$ is independently selected from the group consisting of hydrogen and an alkyl of 1 to 8 carbon atoms, or together with $R^9$ forms an alkylene group of 2 to 8 carbon atoms, with the proviso that, other than in a group of the formula (II), (III) or (IV), X contains no olefinic unsaturation; and each of Y and Z is independently selected from the group consisting of a group of the formula (II), a group of the formula (III) and a group of the formula (IV), and more preferably selected from the group consisting of a group of the formula (II) and a group of the formula (III).

Particularly preferred compounds of the general formula (I) are those wherein:

X is selected from the group consisting of hydrogen, alkyl of 1 to 8 carbon atoms, aryl of 6 to 10 carbon atoms, aralkyl of 7 to 14 carbon atoms, alkoxy of 1 to 8 carbon atoms, aryloxy of 6 to 10 carbon atoms, aralkoxy of 7 to 14 carbon atoms, alkylthio of 1 to 8 carbon atoms, arylthio of 6 to 10 carbon atoms, aralkylthio of 7 to 14 carbon atoms, amido of 1 to 8 carbon atoms, sulfonamido of 1 to 8 carbon atoms, amino ($-NH_2$), monoalkylamino of 1 to 8 carbon atoms, dialkylamino of 2 to 16 carbon atoms, pyrrolidino, piperidino, azepino, morpholino, N-alkylpiperazino, a group of the formula (II), a group of the formula (III) and a group of the formula (IV);

more preferably selected from the group consisting of a group of the formula (II), a group of the formula (III) and a group of the formula (IV), and especially selected from the group consisting of a group of the formula (II) and a group of the formula (III);

A is an alkylene group of 3 to 5 carbon atoms;

$R^1$ is selected from the group consisting of hydrogen and an alkyl of 1 to 4 carbon atoms;

$R^2$ is $-OR^9$;

$R^3$ is selected from the group consisting of hydrogen and an alkyl of 1 to 4 carbon atoms;

$R^4$ is $-OR^{11}$;

D is an alkylene group of 3 to 5 carbon atoms;

$R^5$ is $-OR^9$;

$R^6$ is selected from the group consisting of hydrogen and an alkyl of 1 to 4 carbon atoms;

Q is an alkylene group of 2 to 4 carbon atoms;

$R^7$ is selected from the group consisting of hydrogen and an alkyl of 1 to 8 carbon atoms;

$R^8$ is selected from the group consisting of hydrogen and an alkyl of 1 to 4 carbon atoms;

each $R^9$ is independently selected from the group consisting of hydrogen and an alkyl of 1 to 4 carbon atoms, or together with $R^{11}$ forms an alkylene group of 2 to 8 carbon atoms, each $R^{11}$ is independently selected from the group consisting of hydrogen and an alkyl of 1 to 4 carbon atoms, or together with $R^9$ forms an alkylene group of 2 to 8 carbon atoms, with the proviso that, other than in a group of the formula (II), (III) or (IV), X contains no olefinic unsaturation; and each of Y and Z is independently selected from the group consisting of a group of the formula (II), a group of the formula (III) and a group of the formula (IV), and more preferably selected from a group of the formula (II) and a group of the formula (III).

Process for Preparing the Compounds of the Formula (I) and Compositions Containing Such Compounds The compounds of the formula (I) may be prepared by contacting components (i) and (ii) as earlier described.

In the practice of the process of the invention, contacting may be carried out by adding (ii) to (i) and heating the reaction mixture for a temperature and time sufficient to displace at least two leaving groups present on (i) and substituting therefor at least two groups derived from (ii). In a preferred procedure, (i) and (ii) are initially contacted at temperatures in the range of from about 0° C. to about 50° C. for an initial exothermic reaction, after which the temperature is maintained in the range of from about 50° C. to about 150° C. for the final stages of reaction to effect complete conversion. The reaction time is typically in the range of from about 15 minutes to about 120 minutes for the initial exothermic reaction, and thereafter it is in the range of from about 2 hours to about 24 hours for the final stages of reaction to effect complete conversion.

The 1,3,5-triazine derivatives (i) of the formula (V) are generally known compounds, and preferably include those wherein:

$L^1$ is selected from the group consisting of hydrogen, alkyl, aralkyl, aryl and a leaving group selected from halogen, alkoxy, aralkoxy, aryloxy, alkylthio, aralkylthio, arylthio, amino, amido, sulfonamido and sulfonate, and each of $L^2$ and $L^3$ is independently a leaving group selected from halogen, alkoxy, aralkoxy, aryloxy, alkylthio, aralkylthio, arylthio, amino, amido, sulfonamido and sulfonate.

Especially preferred are those wherein $L^1$, $L^2$ and $L^3$ are each independently a halogen, and particularly chloride (cyanuric chloride).

The nucleophilic reagents (ii) are also generally known compounds as exemplified, for example, in previously incorporated U.S. Pat. No. 4,647,611, U.S. Pat. No. 4,663,410, U.S. Pat. No. 4,691,026, U.S. Pat. No. 4,774,283, U.S. Pat. No. 4,788,288, U.S. Pat. No. 4,814,226, U.S. Pat. No. 4,864,055, U.S. Pat. No. 4,959,489, U.S. Pat. No. 5,298,567, EP-A-0218827, the article by R. K. Pinschmidt, Jr., et al. in Amer. Chem. Soc. Symp. Set., Crosslinked Polymers, Volume 367, page 453 (1988) and the article by K. Kjellqvist et al. in J. Appl. Polym. Science, Volume 51, page 1063 (1994).

As specific examples of compounds of the formula (VI) may be mentioned aminoacetaldehyde dimethyl acetal, aminoacetaldehyde diethyl acetal, aminoacetaldehyde dipropyl acetal, aminoacetaldehyde diisopropyl acetal, aminoacetaldehyde dibutyl acetal, aminoacetaldehyde diamyl acetal, aminoacetaldehyde methylethyl acetal, 3-aminopropionaldehyde dimethyl acetal, 3-aminopropionaldehyde diethyl acetal, 3-aminopropionaldehyde dipropyl acetal, 3-aminopropionaldehyde diisopropyl acetal, 3-aminopropionaldehyde dibutyl acetal, 3-aminopropionaldehyde diamyl acetal, 3-aminopropionaldehyde methylethyl acetal, 4-aminobutryaldehyde dimethyl acetal, 4-aminobutryaldehyde diethyl acetal, 4-aminobutryaldehyde dipropyl acetal, 4-aminobutryaldehyde diisopropyl acetal, 4-aminobutryaldehyde dibutyl acetal, 4-aminobutryaldehyde diamyl acetal, 4-aminobutryaldehyde methylethyl acetal, 5-aminopentanal dimethyl acetal, 5-aminopentanal diethyl acetal, 5-aminopentanal dipropyl acetal, 5-aminopentanal diisopropyl acetal, 5-aminopentanal dibutyl acetal, 5-aminopentanal diamyl acetal, 5-aminopentanal methylethyl acetal, 6-aminohexanal dimethyl acetal, 6-aminohexanal diethyl acetal, 6-aminohexanal dipropyl acetal, 6-aminohexanal diisopropyl acetal, 6-aminohexanal dibutyl acetal, 6-aminohexanal diamyl acetal, 6-aminohexanal methylethyl acetal, 7-aminoheptanal dimethyl acetal, 7-aminoheptanal diethyl acetal, 7-aminoheptanal dipropyl acetal, 7-aminoheptanal diisopropyl acetal, 7-aminoheptanal dibutyl acetal, 7-aminoheptanal diamyl acetal and 7-aminoheptanal methylethyl acetal, as well as hydrated forms thereof (containing —OH groups).

As specific examples of compounds of the formula (VII) may be mentioned 2-methoxypyrrolidine, 2-ethoxypyrrolidine, 2-hydroxypyrrolidine, 2-methoxypiperidine, 2-ethoxypiperidine and 2-hydroxypiperidine.

As specific examples of compounds of the formula (IV) may be mentioned 2,3-dihydropyrrole and 1,2,3,4-tetrahydropyridine.

As indicated above, the compounds of the formula (VI), (VII) and (VIII) may be used as such or in a salt form, such as the hydrohalide salts like the hydrochloride or hydrobromide salt.

The 1,3,5-triazine derivatives of the formula (I) containing the cyclic group of the formula (III) (as well as the cyclic compounds of the formula (VII)) may be additionally prepared by intramolecularly cyclizing the open chain groups of the formula (II) (and compounds of the formula (VI)) in a manner similar to that disclosed in the previously incorporated references (for example, U.S. Pat. No. 4,647,611, U.S. Pat. No. 4,691,026, U.S. Pat. No. 4,788,288 and U.S. Pat. No. 4,864,055).

Preferably, such cyclization may be effected by contacting the compounds containing the open chain groups of the formula (II) (or compounds of the formula (VI) with an anhydrous acid catalyst, typically at room temperature, for a period of time typically in the range of from about 0.5 hours to about 3 hours for complete conversion. Anhydrous acid catalysts usable in this process include acids such as strongly acidic AMBERLYST® 15 ion-exchange resin, sulfonic acids, mineral acids, Lewis acids and the like. The anhydrous process typically retains the alkoxy functionality of $R^2$ and/or $R^3$ (as $R^5$ and/or $R^6$ as the case may be).

Such cyclization may also be effected by contacting the compounds containing the open chain groups of the formula (II) (or compounds of the formula (VI)) with aqueous acid catalysts, typically at room temperature and in the presence of a water miscible solvent such as acetone, dioxane and the like, for a period of time typically in the range of from about 1 hour to about 7 days. Aqueous acid catalysts usable in this process include aqueous solutions of acids such as sulfonic acids, perfluorinated acids, carboxylic acids, phosphoric acids, mineral acids and the like. The aqueous process typically converts at least a portion of the alkoxy functionality of $R^2$ and/or $R^3$ to hydroxyl groups (as $R^5$ and/or $R^6$ as the case may be). For this reason, the aqueous process may not be suitable for compounds wherein both $R^2$ and $R^3$ are alkoxy groups, as both such alkoxy groups may be converted to hydroxyl groups, with the resulting bis-hydroxyl compound being potentially unstable and proceeding further by elimination of water to a carbonyl.

The 1,3,5-triazine derivatives containing the unsaturated cyclic groups ("enamines") of the formula (IV) (as well as the unsaturated cyclic compounds of the formula (VIII)) may be prepared by further reacting the compounds containing the cyclic groups of the formula (III) (and compounds of the formula (VII)) by eliminating the elements of an alcohol or water, as the case may be. As examples of elimination promoters usable in this process may be mentioned the following classes of compounds: carboxylic acid anhydrides, sulfonic acid anhydrides, thionyl halides, sulfuryl halides, phosphorus trihalides, phosphorus pentahalides, phosphorus pentaoxides, phosphorus oxyhalides, molecular sieves, silica gel, alumina, acid catalyst such as ion-exchange resin, sulfonic acids, perfluorinated acids, carboxylic acids, phosphoric acid, mineral acids, Lewis acids, and mixtures thereof.

Products of these Processes

Although the 1,3,5-triazine compounds of the present invention are broadly described in terms of the specific molecular structure of the formula (I), the compositions actually resulting from the above-described processes may in fact, in addition to compounds of the formula (I), include a complex mixture of compounds based on a monomeric or oligomeric 1,3,5-triazine core which is unsubstituted, partially substituted and/or fully substituted with one or more of the groups (II)–(IV). The requirement of the present invention is that such composition comprise on average at least two such groups (which may be the same or different), and preferably on average greater than 2 such groups, per molecule.

For those compounds of the formula (I) wherein X is a leaving group, such as described above for $L^1$, oligomers thereof can be produced by reacting the same with a compound containing active hydrogen groups, such as diols, polyols, diamines and polyamines.

Curable Compositions

An important use of the compounds and compositions described herein is based on their ability to act as crosslinking agents in curable compositions, and especially those curable compositions which contain polyfunctional materials which halve active hydrogen groups. The crosslinkers have on average at least two, and preferably on average more than two, reactive sites of the formula (II), (III) and/or (IV) per molecule, which are capable of crosslinking active hydrogen containing resins.

As previously mentioned, the reactive group in the 1,3,5-triazine derived crosslinking agents of the invention may be open chain (II) or cyclic (III and/or IV), producing crosslinking agents which are open chain, cyclic, or a combination crosslinker having both types of reactive groups. Preferred are those containing at least two groups of the formula (II) and/or (III), with at least a portion of the groups, and preferably a predominant portion of such groups, being of the formula (III). Further, the crosslinking agent may have only two reactive sites such as guanamine derivatives, have three reactive sites such as melamine derivatives, or have more than three reactive sites such as dimeric or higher oligomeric 1,3,5-triazines. All types of the above described 1,3,5-triazine derived crosslinking agents are usable in the curable compositions of the invention.

The polyfunctional material of the curable compositions preferably contains at least one class of a reactive functionality such as hydroxy, carboxy, amino, amido, carbamato, mercapto, or a blocked functionality which is convertible to any of the preceding reactive functionalities. These polyfunctional materials are those which are conventionally used in aminoresin coatings, and in general are considered well-known to those of ordinary skill in the relevant art.

Suitable polyfunctional materials include, for example, polyfunctional hydroxy group containing materials such as polyols, hydroxyfunctional acrylic resins having pendant or terminal hydroxy functionalities, hydroxyfunctional polyester resins having pendant or terminal hydroxy functionalities, hydroxyfunctional polyurethane prepolymers, products derived from the condensation of epoxy compounds with an amine, and mixtures thereof. Acrylic and polyester resins are preferred. Examples of the polyfunctional hydroxy group containing materials include JONCRYL® 500 acrylic resin (S. C. Johnson & Sons, Racine, Wis.), AT-400 acrylic resin (Rohm & Haas, Philadelphia, Pa.), CYPLEX® 1531 polyester resin (Cytec Industries, West Paterson, N.J.), CARGILL® 3000 and 5776 polyester resins (Cargill, Minneapolis, Minn.), TONE® polyester resin (Union Carbide, Danbury, Conn.), K-FLEX® XM-2302 and XM-2306 resins (King Industries, Norwalk, Conn.), CHEMPOL® 11-1369 resin (Cook Composites and Polymers (Port Washington, Wis.), CRYL-COAT® 3494 solid hydroxy terminated polyester resin (UCB CHEMICALS USA, Smyrna, Ga.), RUCOTE® 101 polyester resin (Ruco Polymer, Hicksville, N.Y.), JON-CRYL® SCX-800-A and SCX-800-B hydroxyfunctional solid acrylic resins (S. C. Johnson & Sons, Racine, Wis.), and the like. Examples of carboxyfunctional resins include CRYLCOAT® solid carboxy terminated polyester resin (UCB CHEMICALS USA, Smyrna, Ga.). Suitable resins containing amino, amido, carbamato or mercapto groups, including groups convertible thereto, are in general well-known to those of ordinary skill in the art and may be prepared by known methods including copolymerizing a suitably functionalized monomer with a comonomer capable of copolymerizing therewith.

The curable compositions of the present invention may optionally further comprise a cure catalyst. The cure catalysts usable in the present invention include sulfonic acids, aryl, alkyl, and aralkyl acid phosphates, aryl, alkyl, and aralkyl acid pyrophosphates, carboxylic acids, sulfonimides, mineral acids, and a mixture thereof. Of the above acids, sulfonic acids are preferred when a catalyst is utilized. Examples of the sulfonic acids include benzenesulfonic acid, para-toluenesulfonic acid, dodecylbenzenesulfonic acid, naphthalenesulfonic acid, dinonylnaphthalenedisulfonic acid, and a mixture thereof. Examples of the aryl, alkyl, and aralkyl phosphates and pyrophosphates include phenyl, para-tolyl, methyl, ethyl, benzyl, diphenyl, di-para-tolyl, di-methyl, di-ethyl, di-benzyl, phenyl-para-tolyl, methyl-ethyl, phenyl-benzyl phosphates and pyrophosphates. Examples of the carboxylic acids include benzoic acid, formic acid, acetic acid, propionic acid, butyric acid, dicarboxylic acids such as oxalic acid, fluorinated acids such as trifluoroacetic acid, and the like. Examples of the sulfonimides include dibenzene sulfonimide, di-para-toluene sulfonimide, methyl-para-toluene sulfonimide, dimethyl sulfonimide, and the like. Examples of the mineral acids include nitric acid, sulfuric acid, phosphoric acid, polyphosphoric acid, and the like.

The curable composition may also contain other optional ingredients such as fillers, light stabilizers, pigments, flow control agents, plasticizers, mold release agents, corrosion inhibitors, and the like. It may also contain, as an optional ingredient, a medium such as a liquid medium to aid the uniform application and transport of the curable composition. Any or all of the ingredients of the curable composition may be contacted with the liquid medium. Moreover, the liquid medium may permit formation of a dispersion, emulsion, invert emulsion, or solution of the ingredients of the curable composition. Particularly preferred is a liquid medium which is a solvent for the curable composition ingredients. Suitable solvents include aromatic hydrocarbons, aliphatic hydrocarbons, halogenated hydrocarbons, ketones, esters, ethers, amides, alcohols, water, compounds having a plurality of functional groups such as those having an ether and an ester group, and a mixture thereof.

Preferably, the ratio of the polyfunctional material to the 1,3,5-triazine derived crosslinking agent is in the range of from about 99:1 to about 0.5:1. Overall, the equivalent ratio of the crosslinker to the polyfunctional material is preferably in the range of from about 0.8 to about 1.2. The weight percent of the cure catalyst, if present, is in the range of from about 0.01 to about 3.0 wt % based on the weight of the crosslinker and polyfunctional material components.

An important use of the above-described curable compositions is in the formulation of coating compositions. The present invention is also directed to such coating compositions as well as to methods of coating substrates by applying onto a substrate the coating compositions and heat curing the same.

The present coating compositions may employ a liquid medium such as a solvent, or it may employ solid ingredients as in powder coatings which typically contain no liquids. Contacting may be carried out by dipping, spraying, padding, brushing, rollercoating, flowcoating, curtaincoating, electrocoating or electrostatic spraying.

The liquid or powder coating compositions and a substrate to be coated are contacted by applying the curable composition onto the substrate by a suitable method, for example, by spraying in the case of the liquid compositions and by electrostatic spraying in the case of the powder compositions. In the case of powder coatings, the substrate covered with the powder composition is heated to at least the fusion temperature of the curable composition forcing it to melt and flow out and form a uniform coating on the substrate. It is thereafter fully cured by further application of heat, typically at a temperature in the range of about 120° C. to about 220° C. for a period of time in the in the range of about 5 minutes to about 30 minutes and preferably for a period of time in the range of 10 to 20 minutes. In the case of the liquid compositions, the solvent is allowed to partially evaporate to produce a uniform coating on the substrate. Thereafter, the coated substrate is heated in an oven at a temperature up to about 250° C., for a period of time in the in the range of about 20 seconds to about 14 days and preferably for a period of time in the range of 10 to 45 minutes to obtain a fully cured film. In a particularly advantageous embodiment, coating compositions formulated with crosslinkers containing groups of the formula (III) can be heat cured at lower temperatures preferably ranging from about 50° C. to about 90° C.

The heat cured compositions of this invention may be employed as coatings in the general areas of coatings such as original equipment manufacturing (OEM) including automotive coatings, general industrial coatings including industrial maintenance coatings, architectural coatings, powder coatings, coil coatings, can coatings, wood coatings, and low temperature cure automotive refinish coatings. They are usable as coatings for wire, appliances, automotive parts, furniture, pipes, machinery, and the like. Suitable surfaces include metals such as steel and aluminum, plastics, wood, and glass. The lower temperature curable compositions of the present invention, as described above, are particularly well suited for use to refinish automotive parts and to coat heat sensitive substrates such as plastics and wood which may be altered or destroyed entirely at the elevated cure temperatures prevalent in the heat curable compositions of the prior art.

The crosslinkers of the present invention may also be used as binders for non-wovens, curable compositions containing them may be used as adhesives, and various formulations thereof may be employed to produce crosslinked molded articles.

The following examples illustrate various specific embodiments of the present invention.

EXAMPLE 1

Over a period of one hour, 4-aminobutyraldehyde dimethyl acetal (22.0 g, 0.165 mole) was added dropwise through an addition funnel to a stirred slurry of cyanuric chloride (9.2 g, 0.05 mole), toluene (175 ml), and powdered potassium hydroxide (8.5 g, 0.152 mole) in a 500 ml flask equipped with a reflux condenser, thermometer, nitrogen inlet and mechanical stirrer. The reaction mixture was kept under nitrogen throughout the reaction. The addition rate of the 4-aminobutyraldehyde dimethyl acetal was controlled to maintain the reaction temperature at or below 50° C. (exothermic). After the addition was completed, the slurry was heated under reflux for eight hours, then cooled and filtered. The filtrate was concentrated in vacuo to give a viscous oil which was dissolved in ethyl acetate (250 ml), washed with water, dried over anhydrous sodium sulfate, filtered, and the volatiles removed under vacuum to give a viscous oil (20.0 g, 92.8% isolated yield). The oil was analyzed by infrared (IR), nuclear magnetic resonance (NMR), and mass spectroscopy (MS) and was identified to be the desired 2,4,6-tris-(4,4-dimethoxybutylamino)-1,3,5-triazine: IR (neat, $cm^{-1}$): 3354, 3271, 1566, 1519, 1125, 814; $^1$H NMR ($\delta$): 4.4 (t, 1H), 3.4–3.3 (m, 2H), 3.3 (s, 6H), 1.8–1.6(m,4H); $^{13}$C NMR (ppm): 166, 104, 53, 40, 30, 25; MS (m/e, MH): 475.

EXAMPLE 2

The procedure of Example 1 was repeated with the exception that aminoacetaldehyde dimethyl acetal (6.3 g, 0.060 mole) and cyanuric chloride (3.68 g, 0.02 mole) were used to give 2,4,6-tris-(2,2-dimethoxyethylamino)-1,3,5-triazine as an oily product in 80.8% isolated yield (6.3g). The structure was analyzed by infrared (IR) spectroscopy, and confirmed by NMR spectroscopy $^1$H NMR ($\delta$): 4.2 (t, 1H), 3.6–3.2 (m, 2H), 3.4 (s, 6H).

EXAMPLE 3

This example illustrates solvent-based curable coating composition containing the 2,4,6-tris-(4,4-dimethoxybutylamino)-1,3,5-triazine of Example 1 as the crosslinker, JONCRYL® 500 acrylic resin (S. C. Johnson & Sons) as the polyfunctional material, and CYCAT® 4040 (Cytec Industries Inc.) as the cure catalyst. CYCAT® 4040 cure catalyst is 40 weight % para-toluenesulfonic acid in isopropanol. The amount of CYCAT® 4040 cure catalyst used corresponded to about 0.3 weight % (solids/solids) based on the polyfunctional material plus crosslinker. Toluene was used as the solvent to adjust the solids level of the coating composition to 60 weight %.

| COMPOSITION | Weight (g) |
| --- | --- |
| JONCRYL® 500 acrylic resin | 6.25 |
| 2,4,6-tris-(4,4-dimethoxybutylamino)-1,3,5-triazine | 1.60 |
| CYCAT® 4040 cure catalyst | 0.05 |
| Toluene | 3.10 |

The curable composition was applied to Bonderite® 1000 panels by draw-down (40 mil diameter wire cator) and baked at 180° C. for 20 minutes to give a cured coating having a pencil hardness of F-HB. The solvent resistance was 1/200+ MEK rubs (methyl ethyl ketone double rubs to mar/remove).

EXAMPLE 4

The procedure of Example 3 was repeated with the exception that the catalyst level was increased to 1 weight % (solids/solids). As before, toluene was used as the solvent to adjust the solids level to 60 weight %.

| COMPOSITION | Weight (g) |
| --- | --- |
| JONCRYL® 500 acrylic resin | 6.25 |
| 2,4,6-tris-(4,4-dimethoxybutylamino)-1,3,5-triazine | 1.60 |
| CYCAT® 4040 cure catalyst | 0.17 |
| Toluene | 2.98 |

The composition was applied to Bonderite® 1000 panel by draw-down (40 mil diameter wire cator) and baked at 170° C. for 20 minutes to give cured coating with a solvent resistance corresponding to 50/200+ MEK rubs.

EXAMPLE 5

The procedure of Example 4 was repeated with the exception that the catalyst level was increased to 2 weight % (solids/solids). As before, toluene was used as the solvent to adjust the solids level to 60 weight %.

| COMPOSITION | Weight (g) |
| --- | --- |
| JONCRYL® 500 acrylic resin | 6.25 |
| 2,4,6-tris-(4,4-dimethoxybutylamino)-1,3,5-triazine | 1.60 |
| CYCAT® 4040 cure catalyst | 0.34 |
| Toluene | 2.81 |

The composition was applied to Bonderite® 1000 panel by draw-down (40 mil diameter wire cator) and baked at 160° C. for 20 minutes to give cured coating with a solvent resistance corresponding to 200+/200+ MEK rubs. While the panels baked at higher temperature (180° C.) exhibited some yellowing, there was no yellowing at 160° C. with the present higher catalyst level.

EXAMPLE 6

A solvent based formulation was prepared using the procedure of Example 4 with the 2,4,6-tris-(2,2-dimethoxyethylamino)-1,3,5-triazine of Example 2 as the crosslinker.

| COMPOSITION | Weight (g) |
| --- | --- |
| JONCRYL® 500 acrylic resin | 6.25 |
| 2,4,6-tris-(4,4-dimethoxybutylamino)-1,3,5-triazine | 1.30 |
| CYCAT® 4040 cure catalyst | 0.32 |
| Toluene | 2.63 |

The composition was applied to Bonderite® 1000 substrate panel by draw-down (40 mil diameter wire cator) and baked at 180° C. for 20 minutes. This resulted in a cured coating with 1/200+ MEK rubs with some yellowing.

EXAMPLE 7

A mixture of strongly acidic AMBERLYST® 15 ion-exchange resin (6.6 g), a product of Rohm and Haas Company, Philadelphia, Pa., and methylene chloride (20 ml) in a 100 ml flask equipped with a magnetic stirrer, condenser and nitrogen inlet was stirred for 5 minutes and thereafter, the solvent was removed by decanting. A solution of the 2,4,6-tris-(4,4-dimethoxybutylamino)-1,3,5-triazine of Example 1 (6.1 g, 0.0129 mole) in methylene chloride (120 ml) was then added in one portion to the flask and the resulting mixture was stirred at room temperature under a nitrogen atmosphere for 1.5 hours. The ion exchange resin was then filtered and the volatiles removed under reduced pressure to give 2,4,6-tris-(2-methoxypyrrolidinyl)-1,3,5-triazine (2.7 g, 56% isolated yield) as a glassy solid. The structure of the product was confirmed by nuclear magnetic resonance (NMR) and mass spectroscopic (MS) analysis: $^1$H NMR ($\delta$): 5.6 (m, 1H, —NCHOCH$_3$); 3.8–3.2 (m, 5H, —OCH$_3$ and —NCH$_2$); 2.2–1.6 (m, 4H, —CH$_2$—); $^{13}$C NMR (ppm): 165, 88, 56, 46, 32, 22; MS (m/e, MH): 379.

EXAMPLE 8

This example illustrates the use of the 2,4,6-tris-(2-methoxypyrrolidinyl)-1,3,5-triazine of Example 7 as a crosslinker in a curable solvent based coating composition with JONCRYL® 500 acrylic resin and toluene at 60 weight % solids level. No cure catalyst was used in the formulation. The equivalent ratios of OH to cyclic amino-ether was 1/1.

| COMPOSITION | Weight (g) |
| --- | --- |
| JONCRYL® 500 acrylic resin | 3.00 |
| 2,4,6-tris-(4,4-dimethoxybutylamino)-1,3,5-triazine | 0.63 |
| Toluene | 2.00 |

The composition was applied to Bonderite® 1000 substrate panel by draw-down (40 mil diameter wire cator) and baked at 70° C. for 20 minutes. The composition cured without yellowing producing a coating having good solvent resistance and hardness. The solvent resistance was 200+/200+ MEK rubs and the pencil hardness was F-HB. When baked at 50° C. for 60 minutes, the solvent resistance was 200+/200+ MEK rubs. Similarly, when baked at 50° C. for 20 minutes and thereafter kept at ambient temperatures for 13 days, the coating had a solvent resistance of 200+/200+ MEK rubs.

EXAMPLE 9

Water (50 ml) containing 37 weight % hydrochloric acid (6 ml) was added in one portion to a stirred solution of the tris-(4,4-dimethoxybutylamino)-1,3,5-triazine of Example 1 (6.0 g; 0.0127 mole) in acetone (50 ml) under nitrogen. The reaction mixture was stirred at room temperature for four days and thereafter neutralized with solid potassium carbonate. The solution was then transferred to a separatory funnel and extracted with ethyl acetate (2×150 ml). The organic layer was separated, dried over anhydrous sodium sulfate and the volatiles were removed under reduced pressure to give 2,4,6-tris-(2-hydroxypyrrolidin-1-yl)-1,3,5-triazine as a solid (2.7 g; 64% isolated yield). The structure of the product was confirmed from the $^1$H NMR spectrum which exhibited the characteristic absorption for the —NCHO— group at (δ) 5.6 (m, 1H).

EXAMPLE 10

This example illustrates the use of the 2,4,6-tris-(2-hydroxypyrrolidinyl)-1,3,5-triazine of Example 9 as a crosslinker in a curable solvent based coating composition with JONCRYL® 500 acrylic resin and toluene at 60 weight % solids level. No cure catalyst was used in the formulation. The equivalent ratios of OH to cyclic amino-ether was 1/1.

| COMPOSITION | Weight (g) |
| --- | --- |
| JONCRYL® 500 acrylic resin | 3.10 |
| 2,4,6-tris-(4,4-dimethoxybutylamino)-1,3,5-triazine | 0.56 |
| Toluene | 1.44 |

The composition was applied to Bonderite® 1000 substrate panel by draw-down (40 mil diameter wire cator) and baked at 150° C. for 20 minutes. The composition cured without yellowing producing a coating having good solvent resistance and hardness. The solvent resistance was 1/200+ MEK rubs and the pencil hardness was F-HB.

Although the present invention is described with reference to certain preferred embodiments, it is apparent that modifications and variations thereof may be made by those skilled in the art without departing from the scope of this invention as defined by the appended claims.

We claim:

1. A compound represented by the formula (I):

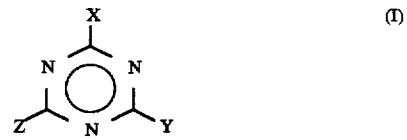

wherein

X is selected from the group consisting of hydrogen, halogen, alkyl, aralkyl, aryl, alkoxy, aralkoxy, aryloxy, alkylthio, aralkylthio, arylthio, amido, sulfonamido, sulfonate, amino, heterocyclic N-containing groups optionally containing a different hetero atom in the ring a group of the formula (II), a group of the formula (III), and a group of the formula (IV)

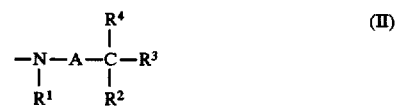

wherein

A is an alkylene group of 1 to 8 carbon atoms, $R^1$ is selected from the group consisting of hydrogen and a hydrocarbyl, $R^2$ is selected from the group consisting of hydrogen, a hydrocarbyl, —$OR^9$ and —$SR^{10}$, $R^3$ is selected from the group consisting of hydrogen, a hydrocarbyl, —$OR^9$ and —$SR^{10}$, and $R^4$ is selected from the group consisting of —$OR^{11}$ and —$SR^{12}$, with the proviso that at least one of $R^2$ and $R^3$ is selected from the group consisting of —$OR^9$ and —$SR^{10}$,

wherein

D is an alkylene group of 3 to 8 carbon atoms, $R^5$ is selected from the group consisting of hydrogen, a hydrocarbyl, —$OR^9$ and —$SR^{10}$, and $R^6$ is selected from the group consisting of hydrogen, a hydrocarbyl, —$OR^9$ and —$SR^{10}$, with the proviso that at least one of $R^5$ and $R^6$ is selected from the group consisting of —$OR^9$ and —$SR^{10}$,

wherein

Q is an alkylene group of 2 to 7 carbon atoms, $R^7$ is selected from the group consisting of hydrogen, a hydrocarbyl, —$OR^9$ and —$SR^{10}$, and $R^8$ is selected from the group consisting of hydrogen and a hydrocarbyl, wherein each $R^9$ is independently selected from the group consisting of hydrogen and a hydrocarbyl, or together with $R^{11}$ forms a hydrocarbylene group,

17 each $R^{10}$ is a hydrocarbyl, or together with $R^{12}$ forms a hydrocarbylene group, each $R^{11}$ is independently selected from the group consisting of hydrogen and a hydrocarbyl, or together with $R^9$ forms a hydrocarbylene group, each $R^{12}$ is a hydrocarbyl, or together with $R^{10}$ forms a hydrocarbylene group, with the proviso that, other than in a group of the formula (II), (III) or (IV), X contains no olefinic unsaturation; and wherein each of Y and Z is independently selected from the group consisting of a group of the formula (II), a group of the formula (III) and a group of the formula (IV).

2. The compound of claim 1, wherein:

X is selected from the group consisting of hydrogen, alkyl of 1 to 8 carbon atoms, aryl of 6 to 10 carbon atoms, aralkyl of 7 to 14 carbon atoms, alkoxy of 1 to 8 carbon atoms, aryloxy of 6 to 10 carbon atoms, aralkoxy of 7 to 14 carbon atoms, alkylthio of 1 to 8 carbon atoms, arylthio of 6 to 10 carbon atoms, aralkylthio of 7 to 14 carbon atoms, amido of 1 to 8 carbon atoms, sulfonamido of 1 to 8 carbon atoms, —$NH_2$, monoalkylamino of 1 to 8 carbon atoms, dialkylamino of 2 to 16 carbon atoms, pyrrolidino, piperidino, azepino, morpholino, N-alkylpiperazino, a group of the formula (II), a group of the formula (III) and a group of the formula (IV);

A is an alkylene group of 1 to 8 carbon atoms;

$R^1$ is selected from the group consisting of hydrogen and an alkyl of 1 to 8 carbon atoms;

$R^2$ is selected from the group consisting of hydrogen, an alkyl of 1 to 8 carbon atoms and —$OR^9$;

$R^3$ is selected from the group consisting of hydrogen, an alkyl of 1 to 8 carbon atoms and —$OR^9$;

$R^4$ is —$OR^{11}$;

with the proviso that at least one of $R^2$ and $R^3$ is a group —$OR^9$;

D is an alkylene group of 3 to 8 carbon atoms;

$R^5$ is selected from the group consisting of hydrogen, an alkyl of 1 to 8 carbon atoms and —$OR^9$;

$R^6$ is selected from the group consisting of hydrogen, an alkyl of 1 to 8 carbon atoms and —$OR^9$;

with the proviso that at least one of $R^5$ and $R^6$ is —$OR^9$;

Q is an alkylene group of 2 to 7 carbon atoms;

$R^7$ is selected from the group consisting of hydrogen, an alkyl of 1 to 8 carbon atoms and —$OR^9$;

$R^8$ is selected from the group consisting of hydrogen and an alkyl of 1 to 8 carbon atoms;

each $R^9$ is independently selected from the group consisting of hydrogen and an alkyl of 1 to 8 carbon atoms, or together with $R^9$ forms an alkylene group of 2 to 8 carbon atoms, each $R^{11}$ is independently selected from the group consisting of hydrogen and an alkyl of 1 to 8 carbon atoms, or together with $R^9$ forms an alkylene group of 2 to 8 carbon atoms, with the proviso that, other than in a group of the formula (II), (III) or (IV), X contains no olefinic unsaturation; and each of Y and Z is independently selected from the group consisting of a group of the formula (II), a group of the formula (III) and a group of the formula (IV).

3. The compound of claim 2, wherein only one of only one of $R^2$ and $R^3$ is a group —$OR^9$, only one of only one of $R^5$ and $R^6$ is a group —$OR^9$, and $R^7$ is selected from hydrogen and an alkyl of 1 to 8 carbon atoms.

18

4. The compound of claim 3, wherein A is an alkylene of 3 to 8 carbon atoms, D is an alkyelene of 3 to 8 carbon atoms, and Q is an alkylene of 2 to 7 carbon atoms.

5. The compound of claim 4, wherein A is an alkylene of 3 to 5 carbon atoms, D is an alkyelene of 3 to 5 carbon atoms, and D is an alkylene of 2 to 4 carbon atoms.

6. The compound of claim 1, wherein X is selected from the group consisting of a group of the formula (II), a group of the formula (III) and a group of the formula (IV).

7. The compound of claim 6, wherein X, Y and Z are independently selected from the group consisting of a group of the formula (II) and a group of the formula (III).

8. The compound of claim 1, wherein:

X is selected from the group consisting of hydrogen, alkyl of 1 to 8 carbon atoms, aryl of 6 to 10 carbon atoms, aralkyl of 7 to 14 carbon atoms, alkoxy of 1 to 8 carbon atoms, aryloxy of 6 to 10 carbon atoms, aralkoxy of 7 to 14 carbon atoms, alkylthio of 1 to 8 carbon atoms, arylthio of 6 to 10 carbon atoms, aralkylthio of 7 to 14 carbon atoms, amido of 1 to 8 carbon atoms, sulfonamido of 1 to 8 carbon atoms, —$NH_2$, monoalkylamino of 1 to 8 carbon atoms, dialkylamino of 2 to 16 carbon atoms, pyrrolidino, piperidino, azepino, morpholino, N-alkylpiperazino, a group of the formula (II), a group of the formula (III) and a group of the formula (IV);

A is an alkylene group of 3 to 5 carbon atoms;

$R^1$ is selected from the group consisting of hydrogen and an alkyl of 1 to 4 carbon atoms;

$R^2$ is —$OR^9$;

$R^3$ is selected from the group consisting of hydrogen and an alkyl of 1 to 4 carbon atoms;

$R^4$ is —$OR^{11}$;

D is an alkylene group of 3 to 5 carbon atoms;

$R^5$ is —$OR^9$;

$R^6$ is selected from the group consisting of hydrogen and an alkyl of 1 to 4 carbon atoms;

Q is an alkylene group of 2 to 4 carbon atoms;

$R^7$ is selected from the group consisting of hydrogen and an alkyl of 1 to 8 carbon atoms;

$R^8$ is selected from the group consisting of hydrogen and an alkyl of 1 to 4 carbon atoms;

each $R^9$ is independently selected from the group consisting of hydrogen and an alkyl of 1 to 4 carbon atoms, or together with $R^{11}$ forms an alkylene group of 2 to 8 carbon atoms, each $R^{11}$ is independently selected from the group consisting of hydrogen and an alkyl of 1 to 4 carbon atoms, or together with $R^9$ forms an alkylene group of 2 to 8 carbon atoms, with the proviso that, other than in a group of the formula (II), (III) or (IV), X contains no olefinic unsaturation; and each of Y and Z is independently selected from the group consisting of a group of the formula (II), a group of the formula (III) and a group of the formula (IV).

9. The compound of claim 8, wherein X is selected from the group consisting of a group of the formula (II), a group of the formula (III) and a group of the formula (IV).

10. The compound of claim 9, wherein X, Y and Z are independently selected from the group consisting of a group of the formula (II) and a group of the formula (III).

11. A composition comprising on average per molecule at least two groups selected from the group consisting of groups of the formula (II), groups of the formula (III) and groups of the formula (IV)

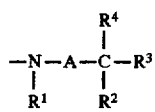 (II)

wherein

A is an alkylene group of 1 to 8 carbon atoms, $R^1$ is selected from the group consisting of hydrogen and a hydrocarbyl, $R^2$ is selected from the group consisting of hydrogen, a hydrocarbyl, —$OR^9$ and —$SR^{10}$, $R^3$ is selected from the group consisting of hydrogen, a hydrocarbyl, —$OR^9$ and —$SR^{10}$, and $R^4$ is selected from the group consisting of —$OR^{11}$ and —$SR^{12}$, with the proviso that at least one of $R^2$ and $R^3$ is selected from the group consisting of —$OR^9$ and —$SR^{10}$,

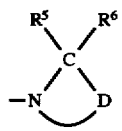 (III)

wherein

D is an alkylene group of 3 to 8 carbon atoms, $R^5$ is selected from the group consisting of hydrogen, a hydrocarbyl, —$OR^9$ and —$SR^{10}$, and $R^6$ is selected from the group consisting of hydrogen, a hydrocarbyl, —$OR^9$ and —$SR^{10}$, with the proviso that at least one of $R^5$ and $R^6$ is selected from the group consisting of —$OR^9$ and —$SR^{10}$,

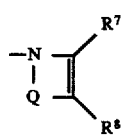 (IV)

wherein

Q is an alkylene group of 2 to 7 carbon atoms, $R^7$ is selected from the group consisting of hydrogen, a hydrocarbyl, —$OR^9$ and —$SR^{10}$, and $R^8$ is selected from the group consisting of hydrogen and a hydrocarbyl, wherein each $R^9$ is independently selected from the group consisting of hydrogen and a hydrocarbyl, or together with $R^{11}$ forms a hydrocarbylene group, each $R^{10}$ is a hydrocarbyl, or together with $R^{12}$ forms a hydrocarbylene group, each $R^{11}$ is independently selected from the group consisting of hydrogen and a hydrocarbyl, or together with $R^9$ forms a hydrocarbylene group, each $R^{12}$ is a hydrocarbyl, or together with $R^{10}$ forms a hydrocarbylene group, prepared by the step of contacting:

(i) a 1,3,5-triazine derivative represented by the formula (V) or an oligomer thereof:

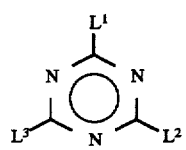 (V)

wherein $L^1$ is selected from the group consisting of hydrogen, halogen, alkyl, aralkyl, aryl, alkoxy, aralkoxy, aryloxy, alkylthio, aralkylthio, arylthio, amido, sulfonamido, sulfonate, amino and a leaving group not previously mentioned, and each of $L^2$ and $L^3$ is independently a leaving group; and (ii) a nucleophilic reagent selected from the group consisting of a compound of the formula (VI), a compound of the formula (VII), a compound of the formula (VIII), a salt thereof and mixtures thereof:

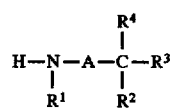 (VI)

wherein A, $R^1$, $R^2$, $R^3$ and $R^4$ are as defined above, with the proviso that at least one of $R^2$ and $R^3$ is selected from the group consisting of —$OR^9$ and —$SR^{10}$,

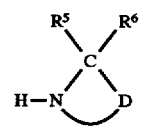 (VII)

wherein D, $R^5$ and $R^6$ are as defined above, with the proviso that at least one of $R^5$ and $R^6$ is selected from the group consisting of —$OR^9$ and —$SR^{10}$,

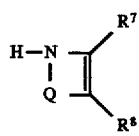 (VIII)

wherein Q, $R^7$ and $R^8$ are as defined above, wherein $R^9$ and $R^{10}$ are as defined above, and wherein said contacting is carried out at a temperature and length of time sufficient to produce a 1,3,5-triazine derivative having thereon on average at least two groups derived from the nucleophilic reagent.

12. The composition of claim 11, wherein:

$R^1$ is selected from the group consisting of hydrogen and an alkyl of 1 to 8 carbon atoms;

$R^2$ is selected from the group consisting of hydrogen, an alkyl of 1 to 8 carbon atoms and —$OR^9$;

$R^3$ is selected from the group consisting of hydrogen, an alkyl of 1 to 8 carbon atoms and —$OR^9$;

$R^4$ is —$OR^{11}$;

with the proviso that at least one of $R^2$ and $R^3$ is a group —$OR^9$;

$R^5$ is selected from the group consisting of hydrogen, an alkyl of 1 to 8 carbon atoms and —$OR^9$;

$R^6$ is selected from the group consisting of hydrogen, an alkyl of 1 to 8 carbon atoms and —$OR^9$;

with the proviso that at least one of $R^5$ and $R^6$ is —$OR^9$;

$R^7$ is selected from the group consisting of hydrogen, an alkyl of 1 to 8 carbon atoms and —$OR^9$;

$R^8$ is selected from the group consisting of hydrogen and an alkyl of 1 to 8 carbon atoms;

each $R^9$ is independently selected from the group consisting of hydrogen and an alkyl of 1 to 8 carbon atoms, or together with $R^{11}$ forms an alkylene group of 2 to 8 carbon atoms, and each $R^{11}$ is independently selected from the group consisting of hydrogen and an alkyl of 1 to 8 carbon atoms, or together with $R^9$ forms an alkylene group of 2 to 8 carbon atoms.

13. The composition of claim 12, wherein only one of only one of $R^2$ and $R^3$ is a group —$OR^9$, only one of only one of $R^5$ and $R^6$ is a group —$OR^9$, and $R^7$ is selected from hydrogen and an alkyl of 1 to 8 carbon atoms.

14. The composition of claim 13, wherein A is an alkylene of 3 to 8 carbon atoms, D is an alkylene of 3 to 8 carbon atoms, and Q is an alkylene of 2 to 7 carbon atoms.

15. The composition of claim 14, wherein A is an alkylene of 3 to 5 carbon atoms, D is an alkylene of 3 to 5 carbon atoms, and Q is an alkylene of 2 to 4 carbon atoms.

16. The composition of claim 11, wherein:

A is an alkylene group of 3 to 5 carbon atoms;

$R^1$ is selected from the group consisting of hydrogen and an alkyl of 1 to 4 carbon atoms;

$R^2$ is —$OR^9$;

$R^3$ is selected from the group consisting of hydrogen and an alkyl of 1 to 4 carbon atoms;

$R^4$ is —$O^{11}$;

D is an alkylene group of 3 to 5 carbon atoms;

$R^5$ is —$OR^9$;

$R^6$ is selected from the group consisting of hydrogen and an alkyl of 1 to 4 carbon atoms;

Q is an alkylene group of 2 to 4 carbon atoms;

$R^7$ is selected from the group consisting of hydrogen and an alkyl of 1 to 8 carbon atoms;

$R^8$ is selected from the group consisting of hydrogen and an alkyl of 1 to 4 carbon atoms;

each $R^9$ is independently selected from the group consisting of hydrogen and an alkyl of 1 to 4 carbon atoms, or together with $R^{11}$ forms an alkylene group of 2 to 8 carbon atoms, and each $R^{11}$ is independently selected from the group consisting of hydrogen and an alkyl of 1 to 4 carbon atoms, or together with $R^9$ forms an alkylene group of 2 to 8 carbon atoms.

17. A composition comprising on average per molecule at least two groups selected from the group consisting of groups of the formula (II) and groups of the formula (III)

(II)

wherein

A is an alkylene group of 1 to 8 carbon atoms, $R^1$ is selected from the group consisting of hydrogen and a hydrocarbyl, $R^2$ is selected from the group consisting of hydrogen, a hydrocarbyl, —$OR^9$ and —$SR^{10}$, $R^3$ is selected from the group consisting of hydrogen, a hydrocarbyl, —$OR^9$ and —$SR^{10}$, and $R^4$ is selected from the group consisting of —$OR^{11}$ and —$SR^{12}$, with the proviso that at least one of $R^2$ and $R^3$ is selected from the group consisting of —$OR^9$ and —$SR^{10}$,

(III)

wherein

D is an alkylene group of 3 to 8 carbon atoms, $R^5$ is selected from the group consisting of hydrogen, a hydrocarbyl, —$OR^9$ and —$SR^{10}$, and $R^6$ is selected from the group consisting of hydrogen, a hydrocarbyl, —$OR^9$ and —$SR^{10}$, with the proviso that at least one of $R^5$ and $R^6$ is selected from the group consisting of —$OR^9$ and —$SR^{10}$, wherein each $R^9$ is independently selected from the group consisting of hydrogen and a hydrocarbyl, or together with $R^{11}$ forms a hydrocarbylene group, each $R^{10}$ is a hydrocarbyl, or together with $R^{12}$ forms a hydrocarbylene group, each $R^{11}$ is independently selected from the group consisting of hydrogen and a hydrocarbyl, or together with $R^9$ forms a hydrocarbylene group, each $R^{12}$ is a hydrocarbyl, or together with $R^{10}$ forms a hydrocarbylene group, prepared by the steps of (a) contacting (i) a 1,3,5-triazine derivative represented by the formula (V) or an oligomer thereof

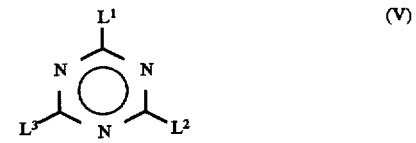
(V)

wherein $L^1$ is selected from the group consisting of hydrogen, halogen, alkyl, aralkyl, aryl, alkoxy, aralkoxy, aryloxy, alkylthio, aralkylthio, arylthio, amido, sulfonamido, sulfonate, amino and a leaving group not previously mentioned, and each of $L^2$ and $L^3$ is independently a leaving group; and (ii) a nucleophilic reagent of the formula (VI) or a salt thereof,

(VI)

wherein A, $R^1$, $R^2$, $R^3$ and $R^4$ are as defined above, with the proviso that at least one of $R^2$ $R^3$ is selected from the group consisting of —$OR^9$ and —$SR^{10}$, wherein $R^9$ and $R^{10}$ are as defined above, at a temperature and for a length of time sufficient to produce a 1,3,5-triazine derivative having thereon on average at least two open-chain groups derived from the nucleophilic agent; then (b) intramolecularly cyclizing at least a portion of the open-chain groups to groups of the formula (III).

18. The composition of claim 17, wherein:

$R^1$ is selected from the group consisting of hydrogen and an alkyl of 1 to 8 carbon atoms;

$R^2$ is selected from the group consisting of hydrogen, an alkyl of 1 to 8 carbon atoms and —$OR^9$;

$R^3$ is selected from the group consisting of hydrogen, an alkyl of 1 to 8 carbon atoms and —$OR^9$;

$R^4$ is —$OR^{11}$;

with the proviso that at least one of $R^2$ and $R^3$ is a group —$OR^9$;

$R^5$ is selected from the group consisting of hydrogen, an alkyl of 1 to 8 carbon atoms and —$OR^9$;

$R^6$ is selected from the group consisting of hydrogen, an alkyl of 1 to 8 carbon atoms and —$OR^9$;

with the proviso that at least one of $R^5$ and $R^6$ is —$OR^9$;

each $R^9$ is independently selected from the group consisting of hydrogen and an alkyl of 1 to 8 carbon atoms, or together with $R^{11}$ forms an alkylene group of 2 to 8 carbon atoms, and each $R^{11}$ is independently selected from the group consisting of hydrogen and an alkyl of 1 to 8 carbon atoms, or together with $R^9$ forms an alkylene group of 2 to 8 carbon atoms.

19. The composition of claim 18, wherein only one of only one of $R^2$ and $R^3$ is a group —$OR^9$, and only one of only one of $R^5$ and $R^6$ is a group —$OR^9$.

20. The composition of claim 19, wherein A is an alkylene of 3 to 8 carbon atoms, and D is an alkylene of 3 to 8 carbon atoms.

21. The composition of claim 20, wherein A is an alkylene of 3 to 5 carbon atoms, and D is an alkylene of 3 to 5 carbon atoms.

22. The composition of claim 17, wherein:

A is an alkylene of 3 to 5 carbon atoms;

$R^1$ is selected from the group consisting of hydrogen and an alkyl of 1 to 4 carbon atoms;

$R^2$ is —$OR^9$;

$R^3$ is selected from the group consisting of hydrogen and an alkyl of 1 to 4 carbon atoms;

$R^4$ is —$OR^{11}$;

D is an alkylene of 3 to 5 carbon atoms;

$R^5$ is —$OR^9$;

$R^6$ is selected from the group consisting of hydrogen and an alkyl of 1 to 4 carbon atoms;

each $R^9$ is independently selected from the group consisting of hydrogen and an alkyl of 1 to 4 carbon atoms, or together with $R^{11}$ forms an alkylene group of 2 to 8 carbon atoms, and each $R^{11}$ is independently selected from the group consisting of hydrogen and an alkyl of 1 to 4 carbon atoms, or together with $R^9$ forms an alkylene group of 2 to 8 carbon atoms.

\* \* \* \* \*

UNITED STATES PATENT AND TRADEMARK OFFICE
CERTIFICATE OF CORRECTION

PATENT NO. : 5,672,703
DATED : September 30, 1997
INVENTOR(S) : Subban Ramesh, Laurence Lyman Williams, Ram Baboo Gupta, Lon-Tang Wilson Lin It is certified that error appears in the above-identified patent and that said Letters Patent is hereby corrected as shown below:

Column 16, line 24, change "t0" to --to--.

Column 17, line 53, change "$R^9$" to --$R^{11}$--.

Column 21, line 49, 5th word, change "(III)" to --(II)--.

Column 22, line 9, change "t0" to --to--.

Signed and Sealed this

Ninth Day of December, 1997

Attest:

BRUCE LEHMAN

Attesting Officer

Commissioner of Patents and Trademarks